United States Patent [19]

Kawahara et al.

[11] 4,086,701

[45] May 2, 1978

[54] DEVICE FOR IMPLANTING AN ARTIFICIAL ENDOSSEOUS ELEMENT OF CERAMICS AND AN IMPLANT METHOD FOR USE OF THE SAME

[75] Inventors: Haruyuki Kawahara, Moriguchi; Masaya Hirabayashi, Yokaichi, both of Japan

[73] Assignee: Kyoto Ceramic Kabushiki Kaisha, Kyoto, Japan

[21] Appl. No.: 674,688

[22] Filed: Apr. 7, 1976

[30] Foreign Application Priority Data

Apr. 7, 1975 Japan .................................. 50-42664
Apr. 16, 1975 Japan .................................. 50-46814

[51] Int. Cl.² .......................................... A61C 13/22
[52] U.S. Cl. ................................................. 32/10 A
[58] Field of Search ...................................... 32/10 A

[56] References Cited

U.S. PATENT DOCUMENTS

| 2,210,424 | 8/1940 | Morrison | 32/10 A |
| 2,835,035 | 5/1958 | Rauscher | 32/10 A |
| 3,499,222 | 3/1970 | Linkow et al. | 32/10 A |
| 3,955,280 | 5/1976 | Sneer | 32/10 A |

FOREIGN PATENT DOCUMENTS

| 1,075,793 | 2/1960 | Germany | 32/10 A |
| 2,401,323 | 7/1974 | Germany | 32/10 A |
| 1,083,769 | 3/1965 | United Kingdom | 32/10 A |

*Primary Examiner*—Robert Peshock
*Attorney, Agent, or Firm*—Spensley, Horn & Lubitz

[57] ABSTRACT

This invention is directed to a device for implanting an artificial endosseous element of ceramics in the field of dentistry, oral surgery and orthopedics, comprising an implant screw pin and a flange member or flange members. The present invention provides an implant element which is adapted for uses of prosthesis even in cases where a hole remains after extraction of a tooth or the bone tissues are unhealthy, and presents an implant pin which is adapted to be securely held by means of the flange member to the tissue of the jaw bone. This invention is also directed to an implant method for use of such device.

8 Claims, 8 Drawing Figures

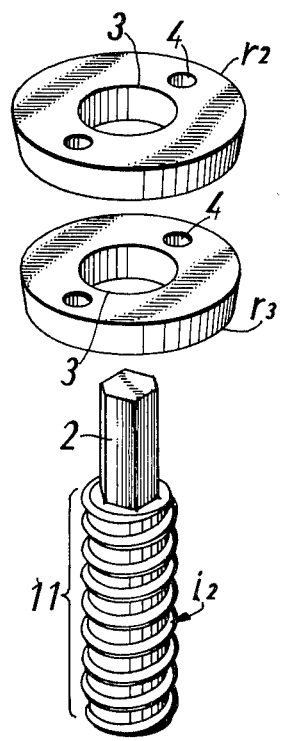
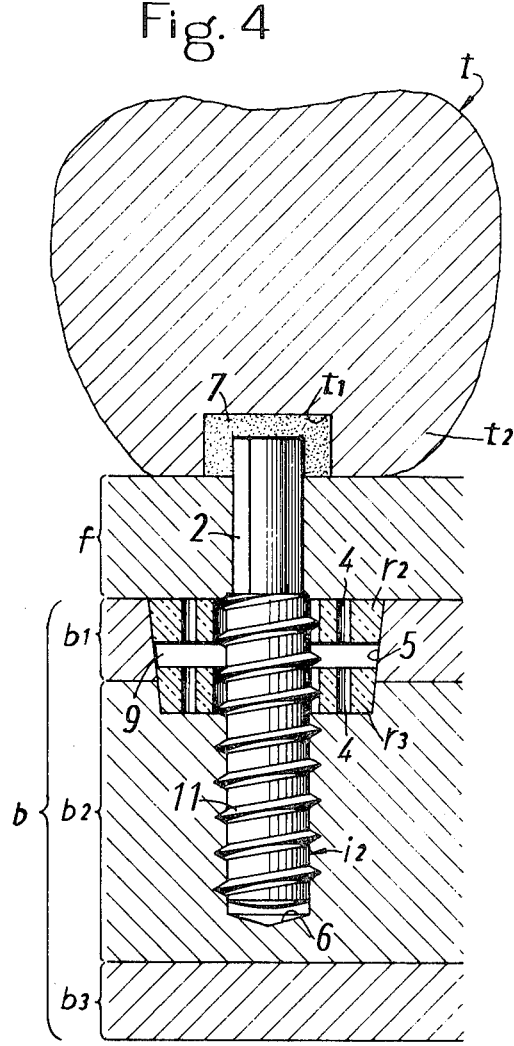

DEVICE FOR IMPLANTING AN ARTIFICIAL ENDOSSEOUS ELEMENT OF CERAMICS AND AN IMPLANT METHOD FOR USE OF THE SAME

BACKGROUND OF THE INVENTION

1. Field of the Invention

The present invention relates to a device for implanting an artificial endosseous element of ceramics in the field of dentistry, oral surgery and orthopedics, and to a method of implanting the same.

2. Prior Art

In accordance with recent trends of development of bio-engineering, implantation of artificial bio material into the bone tissue of a living body has become popular. For instance, a dental implantation technique has been developed, wherein in order to compensate for the loss of natural teeth, an artificial tooth or implant is implanted or inserted into the endosseous or subperiosteal portion of the jaw as a substitute for a clasp abutment tooth of a cantilevered bridge or an abutment tooth of a fixed bridge. The artificial tooth or teeth thus implanted by the implantation technique is called an implant crown, an implant bridge, or an implant denture.

As for the type of endosseous implant in the field of dentistry and oral surgery, the pin, blade and screw varieties are well known.

As for the material of implant, compared with the conventional metal materials such as Co-Cr alloy, Ni-Cr alloy and Ti, ceramics have excellent compatibility with the surrounding tissues and also are quite stable biologically as well as physically and chemically. Thus, ceramics are considered the best material for implant material. However, ceramic implants of the prior art are likely to be damaged by biting stress since these ceramic implants are not known for being mechanically strong and durable compared with those made with metal. More specifically, in an implant in the field of dentistry, compensation for the loss of natural teeth is facilitated by screwing a screw-type implant in the endosseous or subperiosteal portion of the jaw and fixing an artificial tooth to the upper portion of the implant pin wherein the implant pin is implanted in the jaw bone only by the screwing connection between the implant pin and the jaw bone. The lower main portion of the implant pin is screwed into the soft tissue of the jaw bone such that due to the loose screw relation thereinbetween, the connecting relation between the implant pin and the jaw bone may become loose when repeated biting stresses are imparted thereto resulting in instability of the implant pin. Instability of the implant pin may destroy the entire device and prevent the growth of the surrounding tissue and may also cause atrophy. A pocket (p) may become enlarged as a result of the bone atrophy, whereupon the implant screw pin becomes more unstable even to the point of causing the implant screw pin to drop out thus reducing the pocket (p) to a nest of bacilli. Another problem of conventional implants is that there exists a constructional problem in that the screw of the implant pin must be supportable against the external forces as well as be a connecting medium connecting the implant pin with the bone tissue. Given this wide scope of consideration, in order to obtain an implant pin which is universal, the design of the screw of the implant pin such as the outer diameter of the screw, pitch of the threads of the screw and the length thereof are critical. This holds true not only in the implant in the dental field but also to that in oral surgical field.

One solution to the above problem is described in a previously filed application, U.S. Ser. No. 550,186 filed on Feb. 18, 1975 and now Pat. No. 4,016,651 issued Apr. 12, 1977, in which one means to solve the above-described problem is provided. The present invention is a further improvement thereon. In the previous invention, a ceramic implant pin which has a main screw portion to be screwed into the jaw bone and a protruded screw portion which protrudes above the jaw bone from the upper surface of the hard tissue is disclosed. In this device, both screw portions are integrally connected with threads provided on the external circumferences thereof. In addition, a ceramic nut element is screwed into the protruded screw portion until the underside of the nut element is pressed into contact with the surface of the hard tissue of the jaw so that the tight screwing relationship between the implant pin and the hard tissue (jaw bone) can be maintained by tightening the nut element. Accordingly, this previous invention discloses an endosseous implant pin and the technique of implantation by which stability of the implant pin to the biting stress is achieved.

The technique relevant to the prior art is adapted to tightly connect the underside of the nut element to the jaw bone and particularly to the upper surface of the hard tissue. In this technique, the jaw bone functions effectively as a support base to the nut element when the jaw bone is fresh and healthy and good growth of the bone can be expected. However, if the bone tissue is infected by bacilli or bone atrophy, the jaw bone does not function as an effective support base and growth of the bone cannot be expected. In such cases, in prosthesis by use of the implant of the previous invention, boring processes should be required for the jaw until fresh and healthy bone tissue appears by removing unhealthy bone tissue. Unfortunately, due to a hollow formed by the boring process, an implant pin implanted into the jaw bone may become unstable because it is not supportable and so the implant of the previous invention cannot be used when such a situation is presented. This also holds true in the case where the implant pin is implanted for a patient after extraction of a tooth since the extraction hole remains in the jaw bone.

BRIEF SUMMARY OF THE INVENTION

Therefore, the present invention has the objects similar to those of the prior invention but aims to provide an implant element which is able to act as a prothesis even in cases where an extraction hole remains after extraction of a tooth or because of a hole created due to unhealthy bone tissues.

Therefore, one of the objects of the present invention is to provide an implant element which is excellent in stability to the biting stresses.

Another object of the present invention is to provide an implant element of easy implantation techniques.

Still another object of the present invention is to provide an implant element in which growth of the surrounding tissues after implantation is excellent and does away with pocket formations.

Yet still another object of the present invention is to provide an implant element which is endurable for a long period of time.

A further object of the present invention is to provide an implant element which can be implanted immediately after extraction of a tooth without the need for awaiting restoration of the surrounding tissues.

A still further object of the present invention is to provide an implant element which can be implanted even if the bone tissues are infected by bacilli or there exists unhealthy bone tissue by the proceeding atrophy.

These and other objects and advantages will become more apparent from the following description of the invention by way of the preferred embodiments.

BRIEF DESCRIPTION OF THE DRAWINGS

Four preferred embodiments with the examples of the implant in the field of dentistry of the invention are described hereinafter with reference to the accompanying drawings in which:

FIGS. 1 and 2 show the first embodiment of the invention wherein

FIG. 2 is a longitudinal cross-section showing the prosthesis of an artificial tooth using the implant element shown in FIG. 1;

FIGS. 3 and 4 show the second embodiment of the present invention wherein FIG. 3 is a perspective view of another screw-type implant pin and two larger and smaller washer-like flange members;

FIG. 4 is a longitudinal front view showing the prosthesis of the present invention in using the implant element shown in FIG. 3;

FIGS. 5 and 6 show the third embodiment of the present invention wherein FIG. 5 is a perspective view of an implant element which has an integrally mounted flange element, FIG. 6 is a longitudinal front view showing the use of the implant element of FIG. 5.

DETAILED DESCRIPTION OF THE PRESENT INVENTION

Figure 1A:
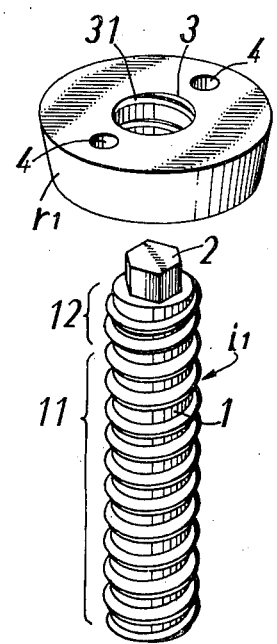
FIG. 1(a) is a perspective view of an implant element comprising a screw-type implant pin.

As is apparent from FIGS. 1 and 2, the first embodiment of the present invention shows a screw implant pin $(i_1)$ provided with an external screw-type configuration 1 in which a portion 11 (hereinafter referred to as the main screw portion) is adapted to be screwed into the jaw bone $(b)$ and in which a portion 12 (hereinafter referred to as the protruded screw portion) is adapted to be protruded from the upper surface of the jaw bone $(b)$ wherein the pin $(i)$ is screwed into the bone. The portions 11 and 12 are generally formed simultaneously by a single screw thread. Numeral 2 denotes a wrench-attaching portion of a hexagonal pillar shape formed at the top of the implant pin $(i_1)$.

A washer-like flange member $(r_1)$ is adapted as a support base of the above-described implant pin $(i_1)$, which washer-like flange member $(r_1)$ being a reversed truncated cone tapered with respect to the lower direction. The cone has an insert hole 3 at the center thereof for securing it to the implant pin $(i_1)$. On the inner wall of the insert hole 3, threads 31 are provided, which threads correspond with those of the main screw portion 11 of the implant pin $(i_1)$. In addition, the washer-like flange member $(r_1)$ is provided with a screwdriver fixing slot members 4 for rotating the flange member.

Figure 1B:
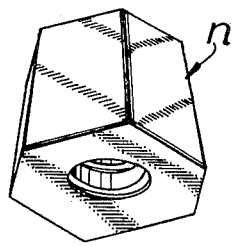
FIG. 1(b) is a perspective view of a nut element used in combination with the implant device.
Figure 2:
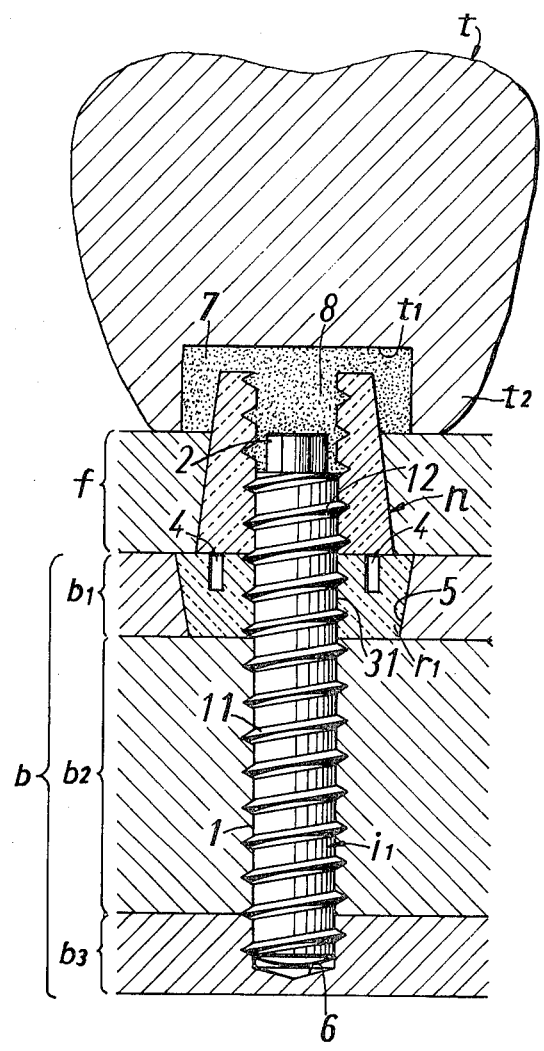

The nut element $(n)$ shown in FIG. 1(b) is screwed onto the protruded screw portion 12 of the implant pin $(i)$ and an artificial tooth is adapted to be fixed to the upper portion of the nut element $(n)$. In FIG. 1(b), the nut element $(n)$, the periphery of which is truncated so as to form a hexagonal pyramid type structure, is tapered in a downward and lower direction. This is for the purpose of enabling easy operation in pressing or striking the artificial tooth in order to fix it to the upper portion of the nut element $(n)$.

The configuration of the present invention with respect to a jaw is described with reference to FIG. 2. In this figure, an artificial tooth $(t)$ is disposed about the implant pin $(i_1)$ and a washer-like flange member $(r_1)$ is shown as being inserted into the jaw member $(b)$. At first, a gingival tissue $(f)$ of a tooth extraction section is incised. A hollow 5 is then made by a boring process to the circumferential portion of a tooth extraction hole (not shown) in the jaw bone (only a hard tissue $(b_1)$ in the case of the exemplified drawing). The hollow 5 is tapered with respect to the lower direction in correspondence with the circumference of the washer-like flange member $(r_1)$. A tapered hole 6 is axially disposed in the hollow 5 to correspond with the main screw portion 11 such that the screw portion may be screwed into the bone of the implant pin $(i_1)$ at the center of the hollow 5.

Thereafter, a wrench is fitted into the wrench-attaching portion 2 of the implant pin $(i_1)$ to rotate it in order to implant the implant pin $(i_1)$ into the jaw bone $(b)$. In this manner, the lower end of the screw portion 11 may reach a hard tissue $(b_3)$ at the lower side of the jaw bone, while the upper portion of the pin $(i_1)$, namely, a protruded screw portion 12, may be left protruding from the upper surface of the jaw bone so as to be susceptible to the nut element $(n)$.

Then, the washer-like flange member $(r_1)$ is fixed so as to proceed upward from the implant pin $(i_1)$ by rotating the screwdriver fixed to the screwdriver-fixing slots 4. Thus, the washer-like flange member $(r_1)$ is fixed tightly in the hollow 5 in the hard tissue $(b_1)$ of the jaw bone. At this stage, the washer-like flange member $(r_1)$ is tightened even after the circumference thereof come into contact with the inner wall of the hollow 5 whereby the implant pin $(i_1)$ screwed in the jaw bone $(b, b_2$ and $b_3)$ is pulled upward by the proceeding of the threads of the washer-like flange member $(r_1)$. This results in the male threads of the main screw portion 11 and the female threads of the tapered hole 6 to be tightly abutted whereby the implant pin $(i_1)$ and the jaw bone $(b, b_2$ and $b_3)$ can maintain a tight screw relationship thus removing the unstable tendency of the implant pin $(i_1)$. After this is achieved, the nut element $(n)$ is screwed onto the protruded screw portion 12 of the implant pin $(i_1)$. At this stage, the nut $(n)$ is tightened a little more even after the lower side (base portion) of the nut element $(n)$ is brought into contact with the upper side of the washer-like flange member $(r_1)$, whereby the implant pin $(i)$ is moved so as to maintain further tight screwing relationship with the jaw bone. This is done such that the washer-like flange member $(r_1)$, the nut element $(n)$, and the implant pin $(i)$ come into a double locked relationship. After that, the artificial tooth $(t)$ is fixed to the upper portion of the nut element $(n)$. In this configuration, in order to restrict the rotation of the nut element $(n)$ and to enable synthetic connection of the nut element $(n)$ with the artificial tooth $(t)$, an adhesive compound 7 such as cement and amalgam is interposed between a fixed hole ($t_1$) which is grooved in a gingival portion ($t_1$) of the artificial tooth ($t$) and the top portion of the nut element ($n$). Thus, the artificial tooth ($t$) is fixedly secured so as to extend upward from the nut element ($n$). In this case, it is preferable to put some of the abovementioned adhesive compound 7 in the inner hollow 8 without leaving any voids or vacancies. By restricting the rotation of the nut element ($n$) with the adhesive compound 7, the washer-like flange member ($r_1$) is also restricted in its rotation because of its engagement by the lower side of the nut element ($n$). Thus, the prosthesis using the present invention has been described as well as its method of insertion.

As for the most preferable example of the washer-like flange member ($r_1$), a reversed truncated cone body is used. This is one in which the tapering is shown as in FIG. 1(b) from the top thereof where it is smaller than the bottom thereof. However, it is to be understood that other configurations such as a cylindrical body are also applicable. However, it should be noted that the nut should never be inserted such that the section that extends outward is larger of the area since, in the case of of the washer-like flange member ($r_1$), the hollow 5 is formed so as to be also tapered with respect to the lower direction in correspondence with the flange member whereby the washer-like flange member ($r_1$) is held is position. Reversal of the flange member would not enable such securement thereto. In the case of the washer-like flange member of truncated cone tapered with respect to the upward direction, the hollow 5 is formed also tapered with respect to the upward direction in correspondence to the flange member, wherein the washer-like flange member may be rendered slidable down toward the soft tissue ($b_2$) by the pressing force as applied from above. Of course, threads 31 are provided for the insert hole 3 of the washer-like flange member ($r_1$) and thus the screwing of the threads 31 with the main screw portion 11 of the implant pin ($i_1$) causes the sliding down action of the washer-like flange member ($r_1$) to be prevented at least to some degree. However, as shown in FIG. 2, in the case of the washer-like flange member of reversed truncated cone, the circumference of the washer-like flange member ($r_1$) is held by the cupshaped hollow 5 removing the possibility of any sliding down action so that the threads 31 are not required to be provided at the insert hole 3 of the washer-like flange member. In the case of the cylindrical washer-like flange member, the flange member ($r_1$) is not as effectively held in the hollow 5 of the jaw bone ($b$) as compared with the case of the washer-like flange member of reversed truncated cone. However, even if the reversed truncated cone is used, the sliding down action is minimal. In such a case, the threads 31 are preferably provided at the insert hole 3. The insert hole 3 of the washer-like flange member is required to be provided at the center thereof. If the insert hole 3 is provided eccentric, remote from the center, the implant pin ($i_1$) cannot be maintained in a stabilized manner since strain is produced in screwing the washer-like flange member ($r_1$) over the implant pin ($i_1$).

The second embodiment is shown with reference to FIG. 3 which takes the example of the most typical dental endosseous implant and shows the adoption of the present invention to the situation where the soft tissue ($b_2$) of the jaw bone ($b$) is partially infected. The difference of the second embodiment from the first embodiment resides in that the wrench-attaching portion 2 at the top of the implant pin 12 is elongated, and the wrench-attaching member 2 is directly connected to the artificial tooth ($t$) by means of the adhesive compound 7 without using the nut element ($n$). Therefore, only the main screw portion 11 is threaded on the circumference of the screw 1 of the implant pin ($i_2$). Furthermore, in place of one washer-like flange member ($r_1$) of reversed truncated cone in the first embodiment, two larger and smaller washer-like flange members ($r_2$ and $r_3$) are adopted. Similar to the washer-like flange member ($r_1$), the larger and smaller washer-like flange members ($r_2$ and $r_3$) are constructed such that at the center of ceramic disks, with the circumferences thereof tapered with respect to the lower direction respectively, form implant pin insert holes 3 and screwdriver-fixing slots 4. However, unlike the washer-like flange member ($r_1$), threads 31 are not formed on the inner wall of the insert holes 3. The implant pin ($i_2$) is penetrated so as to be fixed through the two washer-like flange members ($r_2$ and $r_3$) in such a manner that the washer-like flange member ($r_3$) of smaller diameter is tightly fixed at the bottom of the hollow 5 of the jaw bone ($b$, $b_1$ and $b_2$), and the washer-like flange member ($r_2$) of larger diameter is tightly fixed at the top of the hollow 5. In this case, a clearance 9 is formed between the washer-like flange members ($r_2$ and $r_3$) and the implant pin ($i_2$). To the hollow 5 is applied a boring process which proceeds until a healthy bone tissue is reached. Owing to the growth operation of the healthy bone tissue, the clearance 9 is filled in postoperation so that the clearance 9 does not inconvenience operation; rather the clearance works to securely stabilize the washer-like flange members ($r_2$ and $r_3$).

Figure 5:
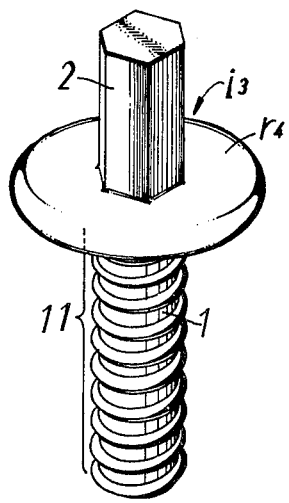
Figure 6:
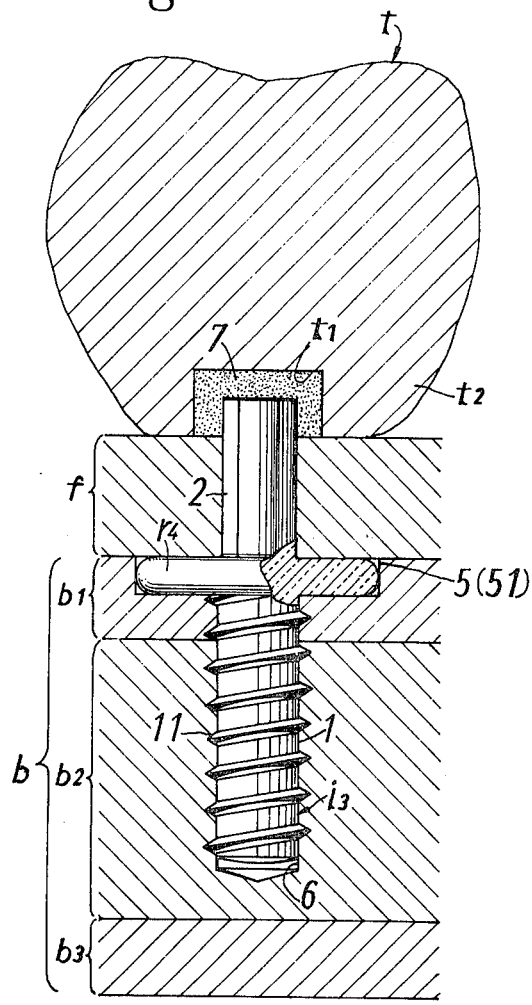

In the third embodiment shown in FIGS. 5 and 6, a screw-type implant pin ($i_3$) is provided, similar to the implant pin ($i_2$) of the second embodiment, on the external circumference thereof, with the screw 1 having the main screw portion 11 threaded and the wrench-attaching portion 2. However, it is different from the implant pin ($i_1$) ($i_2$) of the first and second embodiments in that in this embodiment, a disk-like flange member ($r_4$) for securing the pin is formed horizontally outward on the border circumferences of the screw 1 and the wrench-attaching portion 2, and the flange member ($r_4$) is predeterminately provided integrally with the main portion 11 and the wrench-attaching portion 2. The conditions of prosthesis using the implant pin ($i_3$) is shown in FIG. 6. As shown in FIG. 6, the implant pin ($i_3$) is adapted to be inserted into the jaw bone ($b$) such that, when the implant pin ($i_3$) is screwed in the bone, the flange member ($r_4$) may be tightly fixed in a facing shoulder 51 which is grooved in the hard tissue ($b_1$). In this manner the flange member ($r_4$) functions as a stable base for the implant pin ($i_3$) preventing its unstable tendency.

Figure 7:
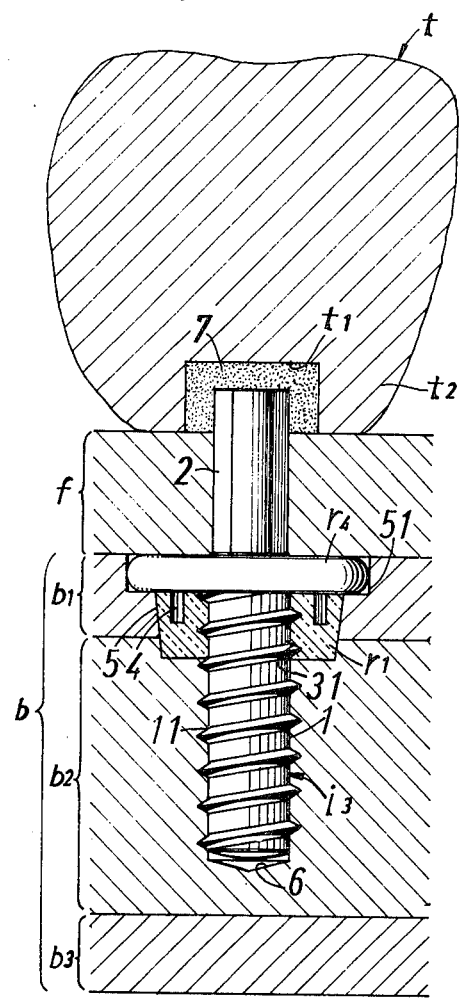
FIG. 7 shows the fourth embodiment of the present invention wherein a longitudinal front view showing the prosthesis of the present invention in using the washer-like flange member of FIG. 1(a) and the implant element of FIG. 5.

The fourth embodiment as shown in FIG. 7 shows prosthesis conditions using the washer-like flange member ($r_1$) of FIG. 1(a) and the implant pin ($i_3$) of FIG. 5. As described hereinabove, in cases where the bone tissues of both the tooth and the jaw bone are infected by bacilli or atrophy, the affected part should be fitted with a boring process up to the bone tissues. A prosthesis condition which enables stable implantation is required even if there exists a hollow formed by the abovementioned boring process. FIG. 7 shows the example of utilizing the present invention for such prosthesis. What is different in this embodiment from the prosthesis condition shown in FIG. 6 is that the washer-like flange member ($r_1$) of reversed truncated cone closely contact the hollow 5 which is smaller in diameter than that of the facing shoulder 51 of the hard tissue ($b_1$). The hollow 5 is disposed deeply in the upper portion of the soft tissue ($b_2$), and the washer-like flange member ($r_1$) is also interposed so that the upper surface thereof corresponds to the lower surface of the facing shoulder 51. The implant pin ($i_3$) of FIG. 5 is screwed into the insert hole 3 having internal threads 31 and the tapered hole 6 pierced at the center of the washer-like flange member ($r_1$) until the flange member ($r_4$) comes into close contact with the lower surface of the facing shoulder 51 and the upper surface of the washer-like flange member ($r_1$) to be implanted. Also in the embodiment of FIG. 7, similar to the embodiment of FIG. 6, the implant pin ($i_3$) is stably secured by the flange member ($r_4$) and further by the washer-like flange member ($r_1$).

As for the material of the implant pin ($i$), the flange member ($r$) and the nut element ($n$), ceramic compositions of matter have better compatibility with the tissues of a living body and also are nontoxic (metal may be toxic) and thus are preferred. However, among ceramic compositions of matter, alumina ceramics is the most preferable. Alumina ceramics has excellent mechanical strength to withstand compression, bending, tensile stresses and impact, and is substantially resistant to the above-mentioned external forces, which is required of the implant element. Thus, Thus, the implant element of alumina ceramics has strong durability with respect to the biting stress and at the same time is physically, chemically and biologically stable. Furthermore, in order to obtain clear opaque images on radiography, the implant pin of alumina ceramics which contains a little bit of more than one metal oxides such as $ZrO_2$, $La_2O_3$ and $Y_2O_3$ has advantageous clinical effect. With respect to the alumina ceramics compositions of matter, prior U.S. Patent Application Ser. No. 524,557 filed on Nov. 18, 1974, may be referred to and is herein incorporated by reference.

Further, the implant pin ($i$) fabricated by monocrystalline alumina ceramics has high strength to the biting stress and is preferable. In the case where the implant pin ($i_3$) is provided integrally with the flange member ($r_4$), the implant pin ($i_3$) and the flange member ($r_4$) are fabricated by the same material. However, in the case where the washer-like flange members ($r_1$, $r_2$ and $r_3$) are fabricated separately from the implant pin ($i$), the flange members ($r_1$, $r_2$ and $r_3$) are preferably fabricated by porous alumina ceramics. This is because the flange member of fine ceramics of impermiability has further compatibility with the bone tissues compared with other material such as metal and plastic, and easy growth of the bone tissue on the surfaces of the washer-like flange members ($r_1$, $r_2$ and $r_3$) is expected. However, the newly grown bone tissues cannot penetrate through the inner portions of the flange members to be secured. On the other hand, the flange members ($r_1$, $r_2$ and $r_3$) of porous material which contacts with the surface of the bone tissue does permit the penetration of newly grown bone tissues through the hollows of the flange members ($r_1$, $r_2$ and $r_3$) easily enabling complex material or synthetic body and living body to be formed between the tissues and the flange members ($r_1$, $r_2$ and $r_3$) resulting in further stable securing of the flange members ($r_1$, $r_2$ and $r_3$). In order to enable penetration of newly grown bone tissues, the present inventors found that the washer-like flange members ($r_1$, $r_2$ and $r_3$) of porous ventilative ceramics having significant openings of 0.2 - 0.7 mm and preferably 0.3 - 0.5 mm of opening diameter at the contact surface with the bone tissue and formed with numerous air passages linked with the significant openings are the most preferable. The ventilative feature is required for dispersing gases ($CO_2$ and $NH_3$ are especially abundant in a living body) which exist innerly in correspondence with the penetration of newly grown bone tissue to the significant openings. By the ventilative feature, the penetration of the newly grown bone tissues to the surfaces of the washer-like flange members ($r_1$, $r_2$ and $r_3$) is further promoted. Of course, the whole of the washer-like flange members ($r_1$, $r_2$ and $r_3$) may be of porous material and in consideration of mechanical strength, the flange members ($r_1$, $r_2$ and $r_3$) may be constructed such that some range of thickness at the surface which is to contact with the bone tissue is porous and the range of thickness inner than the surface is non-porous.

With respect to details of the porous alumina ceramics and the manner of manufacture thereof, U.S. Patent Application filed on Apr. 4, 1975, entitled "Ceramic Endosseous Implant Element Having Porous Contacting Surface and the Method of Manufacturing It" of the same applicant may be referred and is herein incorporated by reference.

The present invention is described hereinabove by way of the preferred embodiments. As already described, the present invention presents an implant pin which is adapted to be securely held by means of the flange member ($r$) which is tightly fixed, under the conditions of the implant pin ($i$) screwed in the bone, in the hollow 5 or the facing shoulder 51 provided at the hard tissue ($b_1$) of the jaw bone. In this manner, the biting stress or other external forces imparted to the implant pin ($i$) afterwards can be diverged mainly by the flange member ($r$) and the implant pin ($i$) so that the external forces transmitted to the screw ($i$) is reduced. This means that any unstable tendency and damage of the implant pin ($i$) after operation can be prevented. Moreover, due to the fact that the implant ($i$) is stably secured, good growth of the surrounding bone tissues of the implant ($i$) is expected, bone atrophy does not occur, the implant ($i$) may not be loose or dropped off, and a pocket of a nest of bacilli is not produced.

Further, even if there exists a tooth extraction hole after extraction of a tooth, or the jaw bone ($b$) is infected up to bone tissues, boring process is given to the jaw bone ($b$) up to the fresh and healthy bone tissue where, notwithstanding a hollow produced by the boring process, the implant pin ($i$) can be implanted to be stably secured in the jaw bone ($b$) according to the first, second and fourth embodiments since the washer-like flange members ($r_1$, $r_2$ and $r_3$) are fixed tightly in the hollow and can maintain fixture of the implant pin ($i$). Thus, as compared with the prior art, the present invention can provide a developed implant technique which can use the implant element of the prior art even in such a case where a tooth extraction hole exists or where the bone tissues of the jaw bone ($b$) are infected, the implant element can be implanted without waiting for the restoration of the surrounding tissues.

In addition, if the implant pin ($i$) is fabricated by mono-crystalline alumina ceramics, resistance to the biting stress is promoted and also if the washer-like flange members ($r_1$, $r_2$ and $r_3$) are fabricated by porous alumina ceramics, penetration of the newly grown bone tissues is enabled through the flange members ($r_1$, $r_2$ and $r_3$) whereby the flange members are further stably secured.

Further, in the case where the main screw portion 11 is provided with threads 31 in the inner wall of the insert hole 3, the main screw portion 11 of the implant pin (i) can still have tight screwing relationship therewith. The implant pin (i) can be securely implanted in the bone, and in addition, to the threads, as with the prior invention. This is achieved by having a nut element (n) screwed onto the protruded screw portion 12 at the upper portion of the implant pin (i).

Also, as described hereinabove, the external forces imparted to the screw 1 of the implant pin (i) can be reduced by the flange member (r) so that the main screw portion 11 of the screw 1 need not be a support medium to the external forces as well as a connecting medium of the implant (i) with the bone tissues. The screw portion only has to function as a connecting medium whereby such factors as support to the external forces need not be required to be considered in designing the pitch of threads, length of the screw, or diameter of the screw and the like.

As for the material of the implant element in the present invention, ceramics is used whereby even if the implant element is left for a long time after implantation, the implant element has good compatibility with the bone tissue and it is non-toxic so that, together with the above-described durability, it can be used semipermanently.

The present invention is herein described taking the example of implant element in the dental field. However, the same advantages of the present invention can be expected in the orthopedic field such as in the treatment of fractured arm, legs and the like or decay in joints. Thus, this invention should not be limited to the dental field.

What is claimed is:

1. A device for implanting an artificial endosseous element into a bone tissue consisting of:
    an implant screw pin;
    a flange member in combination with said pin for securely holding said pin, said pin having external threads on the circumference of a main portion thereof to be screwed directly into the bone tissue, said main portion is adapted to be a main screw portion and being provided with a tool-attaching portion at the top of said main portion;
    said flange member being of burnt ceramics and being anchored in association with said pin into a facing shoulder recessed around said pin, said facing shoulder is predeterminately provided in a hard tissue of the bone, thereby holding said pin tightly in said bone tissue.

2. The device according to claim 1 wherein washer-like flange members are coupled to said flange member, said washer-like flange members being of a generally cylindrical and tapered shape and having an insert hole at the center thereof for fixing to said implant pin.

3. The device according to claim 1 wherein a horizontal flange member integral with said pin is adapted for said flange member.

4. The device according to claim 2 wherein said washer-like flange member has a plurality of significant openings of 0.2 - 0.7 mm and preferably 0.3 - 0.5 mm of opening diameter at the surface contacting with the bone tissue enabling penetration of newly grown bone tissue through said flange member and numerous air passages providing link with said significant openings.

5. The device according to claim 3 wherein said implant pin is fabricated by mono-crystalline alumina ceramics.

6. A method of implanting an artificial endosseous element into a bone structure of a human body for restoring said bone structure to its original configuration consisting of:
    incising a gingival tissue;
    recessing a facing shoulder to receive flange member at a hard tissue of said bone structure;
    forming a tapered hole at the center of said facing shoulder in said bone structure;
    screwing into said tapered hole a ceramic implant screw pin having external threads on a main portion thereof; and
    screwing onto said screw pin a ceramic washer-like flange member formed separate from said pin and having an insert hole provided with threads corresponding to the external threads of said pin in association therewith such that said flange member is anchored into said facing shoulder thereby tightly holding said pin in said bone structure.

7. A device for implanting an artificial endosseous element into a bone structure of a human body for restoring said bone structure to its original configuration consisting of:
    an implant screw pin of ceramics;
    a ceramic flange member in combination with said pin for securely holding said pin; and
    a ceramic nut element,
    said implant pin having external threads on the circumference of a main portion thereof to be screwed directly into bone tissue, which main portion is adapted to be a main screw portion and external threads on the circumference of a protruded portion to be protruded from the upper surface of said bone tissue, which protruded portion is adapted, when said pin is screwed in the bone, to be screwed with said nut element, said protruded portion being provided with a tool-attaching portion at the top thereof,
    said flange member being anchored in association with said pin into a facing shoulder recessed aorund said pin, which facing shoulder is predeterminately provided in a hard tissue of the bone, and
    said nut element being screwed onto said protruded portion of said pin when said implant pin and said flange member are associated.

8. A device for implanting an artificial endosseous element into a bone structure of a human body for restoring said bone structure to its original configuration consisting of:
    an implant screw pin of ceramics; and
    a ceramic washer-like flange member in combination with said pin but fabricated separate therefrom,
    said implant pin having external threads on the circumference of a main portion thereof to be screwed directly into bone tissue, which main portion is adapted to be a main screw portion, a tool-attaching portion at the upper portion of said main portion and a disk-shaped horizontal flange member which is projectably formed horizontally outward on the border circumferences of said main portion and said tool-attaching portion, which disk-shaped horizontal flange member being integral with said main portion and said tool-attaching portion, said washer-like flange member being of reversed truncated cone tapered with respect to the lower direction thereof, having an insert hole provided with threads at the center of said flange member for screwing with said pin and tool-attaching slots for rotating said washer-like flange member and being anchored in association with said pin, when said implant pin is screwed in the bone, into a deep facing shoulder of smaller diameter which is predeterminately provided at the hard tissue of the bone, and said horizontal flange member being anchored into a shallow facing shoulder of larger diameter so that the lower surface of said horizontal flange member is in close contact with the upper surface of said washer-like flange member.

* * * * *